United States Patent [19]
Twardowski et al.

[11] Patent Number: 6,132,616
[45] Date of Patent: Oct. 17, 2000

[54] METHOD FOR FLUSHING AND FILLING OF AN EXTRACORPOREAL BLOOD CIRCULATION SYSTEM OF A DIALYSIS MACHINE

[76] Inventors: Zbylut J. Twardowski, 304 Devine Ct., Columbia, Mo. 65203; Rodney S. Kenley, 816 Fair Way, Libertyville, Ill. 60048

[21] Appl. No.: 08/335,102

[22] Filed: Nov. 7, 1994

Related U.S. Application Data

[62] Division of application No. 08/155,993, Nov. 22, 1993, Pat. No. 5,484,397, which is a division of application No. 07/748,036, Aug. 21, 1991, Pat. No. 5,336,165.

[51] Int. Cl.$^7$ .................................................. B01D 61/00
[52] U.S. Cl. ......................... 210/646; 210/645; 210/805; 210/929
[58] Field of Search ..................... 210/646, 805, 210/929, 645, 806; 604/4, 5, 6, 4.01, 5.01

[56] References Cited

U.S. PATENT DOCUMENTS

| | | |
|---|---|---|
| 3,441,136 | 4/1969 | Serfass et al. . |
| 3,753,493 | 8/1973 | Mellor . |
| 3,871,913 | 3/1975 | Shaldon . |
| 3,920,030 | 11/1975 | Mason . |
| 4,024,059 | 5/1977 | Sausse . |
| 4,399,030 | 8/1983 | Hlavinka et al. . |
| 4,444,597 | 4/1984 | Gortz et al. . |
| 4,517,081 | 5/1985 | Amiot et al. . |
| 4,676,905 | 6/1987 | Nagao et al. . |
| 4,695,385 | 9/1987 | Boag . |
| 4,784,495 | 11/1988 | Jonsson et al. . |
| 5,259,961 | 11/1993 | Eigendorf ................................ 210/646 |
| 5,336,165 | 8/1994 | Twardowski ............................. 604/5 |

FOREIGN PATENT DOCUMENTS 3442744  6/1986  Germany .

OTHER PUBLICATIONS

Operator's Manual for the Gambro MPS–10 System with Continuous Fluid Preparation, Gambro AB, 1987.
B. von Albertini et al. Abstract submitted and made available at the American Society of Nephrology meeting in 1987.
Scribner et al. article entitled Treatment of Chronic Uremia by Means of Intermittent Hemodialysis: A Preliminary Report, ASAIO Transactions 1960 vol. 6, pp. 114–122.
Hegstrom et al. article entitled Two Year's Experience With Periodic Hemodialysis in the Treatment of Chronic Uremia, ASAIO Transactions 1962 vol. 8, pp. 266–275.
Kjellstrand et al. entitled The "Unphysiology" of Dialysis: A Major Cause of Dialysis Side Effects? Kidney International 1975; 7 (Supplement 3) pp. S30–S34.

(List continued on next page.)

*Primary Examiner*—John Kim
*Attorney, Agent, or Firm*—McDonnell Boehnen Hulbert & Berghoff

[57] ABSTRACT

A method for flushing and filling of an extracorporeal blood circulation system of a dialysis machine is disclosed. The machine has a dialyzer, a separate dialysis liquid circuit flowing through a dialysate side of the dialyzer with the extracorporeal blood circulation system flowing through a blood side of the dialyzer for removal of impurities from the blood and the dialysate and blood sides of the dialyzer separated by a hemodialyzer membrane. The method comprises the steps of transporting dialysis liquid from the dialysis liquid circuit in the dialysate side of the dialyzer through the hemodialyzer membrane into the blood side of the dialyzer and the extracorporeal blood circulation system to flush and fill the system and conducting a dialysis treatment.

8 Claims, 2 Drawing Sheets

OTHER PUBLICATIONS

Zbylut Twardowski article entitled The Adequacy of Haemodialysis in Treatment of Chronic Renal Failure, ACTA Med. Pol., 1974, XV, 4 pp. 227–243.

Zbylut Twardowski article entitled Significance of Certain Measurable Parameters in the Evaluation of Haemodialysis Adequacy ACTA Med. Pol., 1974, XV, 4, pp. 245–254.

Zbylut Twardowski article entitled Effect of Long–Term Increase in the Frequency and/or Prolongation of Dialysis Duration on Certain Clinical Manifestations and Results of Laboratory Investigations in Patients With Chronic Renal Failure, ACTA Med. Pol., 1975, XVI, 1, pp. 31–44.

Article by Teschan et al. entitled Daily Dialysis—Applications and Problems, ASAIO Transactions, 1980, vol. XXVI, pp. 600–602.

Hombrouckx et al. entitled Limitations of Short Dialysis are the Indications for Ultrashort Daily Auto Dialysis, ASAIO Transactions 1989, vol. XXXV, pp. 503–505.

Zbylut Twardowski et al. entitled Renal Replacement in the Next Decade, Dialysis and Transplantation vol. 18, No. 12, pp. 688 & 689, Dec., 1989.

METHOD FOR FLUSHING AND FILLING OF AN EXTRACORPOREAL BLOOD CIRCULATION SYSTEM OF A DIALYSIS MACHINE

CROSS REFERENCE TO RELATED APPLICATIONS

This is a division of U.S. application Ser. No. 08/155,993, filed Nov. 22, 1993, now U.S. Pat. No. 5,484,397, which in turn is a division of U.S. application Ser. No. 07/748,036, filed Aug. 21, 1991, now U.S. Pat. No. 5,336,165, issued Aug. 9, 1994.

BACKGROUND OF THE INVENTION

The proposed invention is an artificial kidney system for frequent, typically daily, hemodialysis intended to improve significantly hemodialysis therapy and prognosis, to make home hemodialysis feasible and even attractive to a much broader base of patients, and to decrease the overall cost burden for patients with chronic renal failure.

There are approximately 120,000 patients on dialysis in the United States, almost 400,000 worldwide. Most of them dialyze in hemodialysis centers and approximately 17% are on home peritoneal dialysis with less that 3% on home hemodialysis. In-center hemodialysis is performed three times per week for between two and four hours. The more "physiologic" four times per week dialysis sessions are used only with patients with severe intolerance to three times weekly dialysis, mostly related to cardiovascular instability. Home hemodialysis is also universally performed three times weekly.

It is well accepted in the nephrology community that the optimal frequency of intermittent hemodialysis for chronic renal failure has not yet been established. The first patients treated by Scribner et al., in 1959 (Scribner B H, Buri R, Caner J E Z, Hegstrom R M, Burnell J M: "The treatment of chronic uremia by means of intermittent hemodialysis: a preliminary report." Trans Am Soc Artif Intern Organs 1960; 6: 114–122) received hemodialysis at intervals of five to seven days for 20–24 hours. However, the patients manifested uremic symptoms which could only be relived by increasing the frequency of dialysis (Hegstrom R M, Murrey J S, Pendras J P, Burnell J M, Scribner B H: "Two years experience with periodic hemodialysis in the treatment of chronic uremia." Trans Am Soc Artif Intern Organs 1962; 8: 266–275). Later, in the 1960's, twice weekly dialyses were used routinely. During the 1970's, three times weekly dialyses became more popular as it was realized that the overall results were better than with twice weekly schedule. Presently, two dialysis per week are applied only in patients with well preserved residual renal function. Three dialyses per week is considered a standard schedule in the majority of dialysis centers as it seems to yield an adequate or acceptable clinical status in the majority of patients.

The amount of time consumed by transportation to and from the center, and the dialysis procedure itself, is mostly tolerable for the patients who perform three sessions per week. Consequently, only those patients who experience unbearable intolerance of body fluid volume fluctuations, and the associated symptoms, agree to more frequent (four times weekly) dialysis sessions. For home dialysis patients, more frequent dialysis than three times per week would mean more stress on the relatives who help with set-up and who monitor the patient and, of course, on the patient who does most of the work for set-up, tear-down, and cleaning.

An arteriovenous fistula, either classic or Gore-tex, is the most commonly used method of creating blood access for hemodialysis. For each dialysis session, the fistula must be punctured with large bore needles to deliver blood into, and return blood from, the artificial kidney (dialyzer). The punctures with these large bore needles are painful, even with the use of anesthetics. It is natural that the patients would like to have punctures done as infrequently as possible. Also, there is a general perception (although no proof) that frequent punctures are detrimental to the fistula longevity. Three times weekly dialysis schedule seems to be a reasonable compromise.

Last, but not least, the current Medicare reimbursement schedule for any form of dialysis is based on three hemodialyses per week done in-center. This allows the providers to maintain a small but acceptable profit margin. More frequent dialysis would mean a substantial increase in the providers' cost of treatment and result in a net loss to the provider for any patient receiving more than three treatments per week.

Existing hemodialysis systems consist fundamentally of two halves; one comprising the extracorporeal blood circuit (the blood flow path) and the other comprising the dialysate circuit or flow path. Typically, the entire blood circuit is disposable and comprises: 1) an arterial and venous fistula needle, 2) an arterial (inflow) and venous (outflow) blood line, 3) a hemodialyzer, 4) physiologic priming solutions (saline) with infusion set, and 5) an anticoagulant (heparin or citrate). The arterial needle accesses blood from the patient's fistula and is connected to the arterial blood tubing set, which conveys blood to the dialyzer.

The arterial line comprises: a pumping segment with interfaces to a blood pump (rotary or peristaltic) on the hemodialysis machine, pressure monitoring chambers including tubing which interfaces to pressure transducers on the machine to monitor the pressure pre-pump and/or post pump, inlet ports for saline and anticoagulant, and one or more injection sites for drawing blood or injecting drugs.

The hemodialyzer typically comprises a case which encloses a bundle of hollow fiber semi-permeable membrane. The blood is circulated on one side of the membrane while dialysis solution is circulated on the other, so that the two never come into direct contact. Uremic toxins diffuse out of the blood and into the dialysis solution owing to the concentration gradient. Excess water in the patent's blood enters the dialysate as a result of a pressure gradient. The membrane is made from either cellulose or synthetic polymers.

The venous line and needle carry the newly dialyzed blood away from the dialyzer and back into the patient's circulatory system via a puncture site slightly closer to the heart than the arterial needle site. The venous set is comprised of a pressure monitoring chamber with tubing leading to another pressure transducer in the machine, injection sites, and a segment of tubing which interfaces to an air detection assembly in the machine in order to prevent air emboli during treatment.

Dialysis solution is typically prepared continuously on-line in present-day machines by combining; 1) water which has first been purified by a separate water treatment system and, 2) liquid concentrates of electrolytes. Over the past decade the dialysate concentrates have evolved from a single formulation which contained acetate as the physiologic buffering agent for the correction of circulatory acidosis, to two containers where bicarbonate replaces acetate as the buffering agent, and must be kept separate due to its chemical incompatibility with calcium and magnesium. Two proportioning pumps are therefore required, the first to mix the bicarbonate concentrate with water and the second to proportion this mixture with the concentrated electrolytes to achieve the final, physiologically compatible solution.

The machine continuously monitors the pressure at the blood inlet and outlet sides of the dialyzer (by way of the pressure transducers connected to the blood sets) as well as in the dialysate circuit. Via microprocessors, the system calculates the transmembrane pressure (TMP) which determines the amount of water transmission through the membrane. These machines also have sophisticated means of measuring the amount of dialysis solution entering and dialysate leaving the dialyzer, which allows the calculation of net water removal from the patient (ultrafiltration). By electronically comparing the amount of water entering or leaving the blood with the transmembrane pressure, the system is able to control actively the water removed from the patient to a desired target previously programmed into the system. When low-water-transmission cellulosic membranes are employed, negative pressure must be generated on the dialysate side of the membrane by the machine in order to accomplish sufficient water removal. Because suction may be applied to the dialysate as it transits the dialyzer, it must first be placed under a greater vacuum in a degassing chamber so that air bubbles are not generated within the dialyzer that would cause errors in the calculation of ultrafiltration by the flow sensors and also reduce the efficiency of the dialyzer. On the other hand, when high-water-transmission, synthetic membranes are used, it is frequently necessary to apply positive pressure on the dialysate side to control the rate of ultrafiltration.

In order to understand fully the advantages of the proposed system it is necessary to also understand the existing procedures. The first step in setting up is typically to prepare the dialysate. For the concentrate of electrolytes no preparation is necessary; a hose from the machine is simply inserted into a jug just as it comes from the manufacturer. The bicarbonate, however, is most often bought as a powder because of its instability in solution, and it must first be mixed in a jug with purified water. When the concentrates are ready, the machine is turned on so that the temperature and conductivity have time to come into their safe operating ranges.

Next, all components of the extracorporeal blood circuit are unpacked, connected together using aseptic technique and threaded onto the machine by matching the respective components to their hardware interfaces. The air is primed out of the circuit by connecting sterile normal saline to the arterial tubing set via an IV administration set, and starting the blood pump on the machine. Agitation of the dialyzer is frequently necessary to remove completely the air from it, and this process can take 10–15 minutes. Some practitioners are able to both prime the circuit and rinse the blood back at the end of treatment with a single one liter bag of saline, but most often, two one-liter bags are required.

If the dialyzer is being reused, a chemical sterilizing solution will be present in the dialyzer instead of air, and this must first be rinsed out. In this case, additional steps are required. Once the bulk of the disinfectant and air are primed out of the circuit, the arterial and venous blood lines are usually connected together to form a closed loop. Thereafter, the enclosed solution is recirculated countercurrently to the dialysate, thus causing any remaining contaminants to dialyze across the membrane, into the dialysate, and down the drain. Before the patent can be connected to this primed extracorporeal circuit, the priming fluid must be manually tested for residual sterilizing chemicals (e.g. formaldehyde) by a calorimetric chemical assay to assure they are at safe levels.

At this point the arterial and venous needles are placed in the patient's blood access site, and the pump is started, causing the priming solution to the displaced into a drain container. When blood approaches the venous tubing set, the pump is stopped. The set is connected to the venous needle, and the pump speed is gradually or rapidly elevated to the prescribed value. Blood flow rates of 175–450 ml/min are typical, being limited by the needle size and access anatomy. The faster the blood flow rate, the faster the dialysis procedure can be accomplished, thereby benefitting both patient and physician (as long as water removal rates are tolerable). However, the needles, which in the past have in part determined the allowable blood flow rate, are typically 14–17 gauge, and are already pushing the tolerance of most patients.

The patient is then dialyzed for a period specified by the nephrologist. Every 15–30 minutes the patient is monitored for pulse, temperature, and blood pressure, and the functions of the machine are also noted and recorded on the patient's chart. Monitoring the patient closely, especially for blood pressure, is important because, as previously stated, a significant number of dialysis patients have very fragile cardiovascular systems and about 25% of all hemodialysis procedures result in hypotensive episodes owing to the rapidity of removing in 2–4 hours the fluid which has been accumulated over 2–3 days. Most of the patients have prodromal symptoms before hypotensive episodes but sometimes the episode occurs suddenly, without warning and patient "crashes", losing consciousness. Most of the "crashes" happen during the second half of hemodialysis sessions. The standard treatment for such blood pressure "crashes" is for the nurse of partner to open up the IV administration line connecting the saline bag to the arterial blood set and to infuse the saline in order to improve the patient's circulatory volume and bring the pressure back up. Slower ultrafiltration helps to reduce incidence of crashes. Therefore, my standard practice is to remove no more than one liter of ultrafiltration per hour. The "crashes" are less frequent if controlled ultrafiltration machines are used.

Another common occurrence during hemodialysis happens when the arterial needle sucks up against the interior wall of the blood vessel either because of the suction generated by the blood pump or because the patient changes his/her arm position. This creates excessive negative pressure in the pre-pump segment of the arterial line which, if monitored by the machine, will trip an alarm and shut off the blood pump until someone repositions the needle and/or arm and restarts the pump. This, of course, wastes time and lengthens the procedure. If the pre-pump pressure is not monitored, then as suction increases, the blood flow rate diminishes dramatically and the amount of dialysis expected does not in reality occur. Moreover, the endothelium (internal blood vessel wall lining) is damaged by suction, which predisposes to clotting and reduces fistula longevity.

At the end of the treatment, the arterial needle is removed, the saline line opened, and the pump started in order to flush the blood remaining in the extracorporeal circuit back to the patient. Most patients are very anemic (the kidneys control the production of new red cells) and, therefore, retrieval of as much blood as possible is important. Since flow is always in the same arterial to venous direction through the circuit, some practitioners will insert the arterial needle into the saline bag so the few inches of tubing between the needle and the saline infusion port will also be flushed.

When the blood is mostly out of the extracorporeal circuit, the venous needle is removed from the patient, and a compress is applied to the puncture site until it clots, which may be 10–20 minutes depending on the size of the needles and the degree of systemic anticoagulation at the end of the treatment. At this point, the needles and blood lines are discarded (in biohazard containers) as these components are rarely reused.

The majority of dialyzers are, however, reused. There are numerous procedures for reusing dialyzers both manually and automatically. In centers, special machines for simultaneous multiple dialyzer regeneration are used. Generally the steps are as follows:

1. High flow rate water flush of blood compartment.
2. Force water through the membrane in dialysate compartment to blood compartment direction (reverse ultrafiltration).
3. Removal of residual blood and protein by flushing blood compartment with bleach and/or peroxide.
4. More water flush.
5. Measurement of remaining fiber bundle volume or the ultrafiltration rate as an indicator of remaining dialyzer efficiency.
6. Filing, capping, and storing the dialyzer with a chemical sterilant such as formaldehyde, peracetic acid, or glutaraldehyde.
7. Documenting all of the above and assuring that there is no chance of using a reused dialyzer on a different patient.

Of course, the above procedures must be done in a biohazard environment since there is always the potential for exposure to human blood, and hepatitis and AIDS are relatively prevalent in the dialysis population. Also, the OSHA and EPA stipulate various working environment regulations owing to the hazardous sterilants and cleaning agents used.

Regeneration of dialyzers and lines may be performed on the machine. The Boag U.S. Pat. No. 4,695,385 discloses a cleaning apparatus for dialyzer and lines. The device is permanently or semipermanently connected into the dialysis machine system.

Finally, the dialysis machine plumbing must be periodically cleaned and disinfected. There are two reasons for this. The first relates to the fact that the dialysate has historically not been sterile. From the very beginning of dialysis as a therapy, the dialyzer membrane has been relied upon to be a sterile barrier between dialysate and blood. This is certainly true for whole bacteria, but concern has been growing over the past several years that with the use of synthetic membranes and their more porous structure, pyrogens, or components thereof, may be permeating these membranes and activating inflammatory processes within the patients. This may be exacerbated because the pressure gradient is frequently in the blood-to-dialysate direction when synthetic membranes are used. The second reason is that when bicarbonate containing dialysate is used, calcium carbonate inevitably precipitates and accumulates on the plumbing and must be dissolved with an acidic solution.

Clinically, three dialyses per week are associated with rapid changes in body fluid compartments and in concentrations of all dialyzable solutes. These changes are aptly called "The Unphysiology of Dialysis" (Kjellstrand C M, Evans R L, Petersen R J, Shideman J R, von Hartizsch B, Buselmeier T J: The Unphysiology of Dialysis: A major cause of side effects?" Kidney Int 1975; 7 (suppl3); S30–S34). Many patients have enormous difficulties achieving a "dry" body weight if they accumulate three, four, or more kilograms of fluid between dialyses. Some patients, especially with heart failure, poorly tolerate even a two kilogram fluid weight gain; they are short of breath before dialysis, have muscle cramps and hypotension during dialysis, and feel "washed out" and are extremely weak, needing several hours to "equilibrate" and become functional. Serum concentration of highly toxic potassium frequently reaches dangerous levels (more than seven mEq/L), particularly preceding the first dialysis after a longer interval (weekend). To mention only a few others, calcium and pH are too low before dialysis or too high after dialysis in many patients. Empirically, in many hemodialysis units, these patients are placed on a four times weekly dialysis schedule.

Whereas the normal human kidneys function continuously to produce seamless, gradual changes in total body fluid volume and metabolic waste levels, three times weekly dialysis schedules produce tremendous, unphysiologic fluctuations which yield considerable stress on the patient's systems and undoubtedly affects their prognosis.

Historically, artificial kidneys developed according to the assumption that the machine should be very sophisticated and automated during dialysis and less so for preparation and cleansing. This assumption was valid for long and infrequent dialysis sessions. Compared to the total dialysis time the time for setup and cleansing of the machines was relatively short.

Another artificial kidney feature that has historical background is a proportioning system of producing dialysis solution and delivering it into hemodialyzer. In the early years of hemodialysis only a so called tank system has been used. The machine was provided with a large tank where purified water was premixed with dry chemicals to make dialysis solution, which was warmed and recirculated through the dialyzer dialysate path. Bicarbonate was used as a buffer; $CO_2$ was bubbled through the solution, or lactic acid was added to the solution to prevent calcium/magnesium carbonate precipitation. With inefficient dialyzers a dialysis time of 12 hours or more was used. Warm dialysate was an excellent culture medium for bacterial growth. Long dialysis time magnified the problem. At the end of 11 hour dialysis, even with several changes of dialysis solution in the tank, bacterial growth was staggering (Twardowski Z, Bahyrycz M, Lebek R, Spett J: Zalety plynu dializacyjnego bez glukozy w leczeniuyprzewleklej niewydolnosci nerek. (Advantages of glucose-free dialyzing fluid for hemodialysis treatment in cases of chronic renal failure.) Pol Arch Med Wewn 1973; 50: 1079–1085.). To overcome this problem a proportioning system was invented whereby the solution was being prepared ex tempore from purified water and concentrate. The concentrate contained acetate as the physiologic buffering agent because bicarbonate tended to precipitate with calcium and magnesium if present in the same concentrate.

Gradually more efficient dialyzers were designed, and time of a single dialysis session gradually decreased to 8, 6, 5, 4, 3, and even 2 hours. With very efficient dialyzers, acetate was delivered to the patient in excess of the body ability to metabolize it, which caused cardiovascular instability. An answer to this problem was to return to bicarbonate as a buffer but within an overall design of proportioning system. As mentioned before, because of chemical incompatibility of bicarbonate with calcium and magnesium, two proportioning pumps are required, the first to mix the bicarbonate concentrate with water and the second to proportion this mixture with the concentrated electrolytes to achieve the final, chemically compatible solution.

However, a short daily dialysis session of 1–3 hours offers a possibility of abandoning the proportioning system, which continues to be used out of tradition rather than a necessity.

With short dialysis there is no significant bacterial growth even if the dialysis solution is premixed in a tank from water and dry chemicals with bicarbonate as a buffer, particularly if the solution flows single pass so that spent dialysate is not mixed with fresh dialysis solution. The spent dialysate that contains amino acids, vitamins, and other nitrogen products is a much better medium for bacterial growth than is the dialysis solution containing only electrolytes and glucose.

With daily, in-center hemodialysis, the time and expense now incurred by the patient and by the staff would be greatly magnified. Also, the dialysis facility's capacity for performing this number of incremental treatments would have to be increased, requiring capital expansion. It is therefore economically and logistically infeasible to do daily dialysis for everybody in-center. Consequently, the patient's home is the only practical location for this modality.

Whereas at the end of 1980 there were 5,085 such patients (9.7% of the total dialysis population), at the end of 1987 only 3,580 (3.6% of the total) patients were on home hemodialysis. The home hemodialysis population is expected to decrease further in the future because of the many disincentives to this therapy even at a frequency of three times per week. Increasing the frequency would only exacerbate most of the following disadvantages:

a: Current equipment is big, complicated, intimidating, and difficult to operate, requiring a very long time for training. Also, both partner and patient must be trained and this represents a major expense to the medial provider.

b: Complication of equipment engenders reliability issues. If a hemodialysis system breaks down in a patient's home, no dialysis is possible until it is repaired.

c: It is currently very difficult for home hemo patients to travel since the present systems are in no way portable.

d: If the bicarbonate component of the dialysate is used in powdered form, it must be mixed and inspected by the patient.

e: Supplies require a large storage space.

f: There is a high initial investment in the dialysis equipment, the water treatment system, and their instillation with low utilization (one patient only) compared to in-center use where the systems are used on many patients.

g: There is little or no possibility for reuse of supplies, providing less economic incentive to the medical sponsor.

h: a partner is required to insert fistula needles and monitor emergencies.

i: Considerable time is involved for setup, priming, tear down, and cleaning.

j: The water treatment system must also be cleaned/disinfected periodically.

Because of the above mentioned disincentives, only highly motivated patients and partners undertake the drudgery of home hemodialysis.

Development of a transcutaneous blood access catheter not requiring needle punctures for each dialysis is currently underway and is described in Twardowski Z J, Van Stone J C, and Nichols W K: Multiple Lumen Catheter for Hemodialysis, as described in U.S. patent application Ser. No. 461,684, filed on Jan. 8, 1990, assigned to the Curators of the University of Missouri. Such an access device further opens the feasibility of daily hemodialysis.

DESCRIPTION OF THE INVENTION

The features of a new system that overcomes the aforementioned problems which currently prohibit daily home hemodialysis are as follows:

1. Built-in water treatment system

For a home (single) dialysis patient a built-in water treatment system instead of a separate unit is both portable and economical.

2. Automated Formulation of Batch Dialysis Solution

For the short, daily dialysis procedures herein proposed, bacterial overgrowth is not a problem, and proportioning systems to manufacture the dialysis solution on-line would no longer be needed. The typically bicarbonate-based dialysis solution should be prepared from mostly dry chemicals and low volume concentrates automatically mixed with treated water in a simple, small batch. The elimination of proportioning systems significantly simplifies machine design and reduces its cost. Use of dry chemicals instead of concentrates lowers transportation cost, considerably decreases requirements for storage space, and lessens the burden on patients.

3. Automated Reuse

The dialyzer and total extracorporeal blood circuit must be reused to keep the cost of treatment as low as possible. Fortunately, there is a wealth of evidence supporting the fact that the reuse of dialyzers does not constitute any additional hazard to the patients. Moreover, some available data suggests that the reused dialyzers are better tolerated by the patients than those used only once. In addition, if reuse is done automatically by the machine, without patient or partner involvement, the burden on their lifestyle will be reduced to attractive levels.

4. Automated Set-up

With daily dialysis, automatic set-up of the machine is important. This must include a reusable extracorporeal blood circuit assembly and automation of the priming of the circuit with sterile, physiologic solution, in order to minimize the time and effort requirements.

5. Automated tear down

The whole process of blood and dialysate circuit cleaning and sterilizing is to be automated.

6. Reduction of storage space requirement

Reuse of dialyzers and lines as well as use of mostly dry chemicals instead of concentrates will reduce the need for storage space.

7. Decrease of elimination of partner involvement

A needle-less system, and an ultrashort dialysis with reduction of dialysis associated symptoms, plus automated set-up and tear down, should eliminate partly or totally partner involvement. Optionally, a remote electronic monitoring of the machine and of the patient's vital signs may be used to augment the safety of the procedure.

8. Reduced training time

A compact, user friendly machine will reduce training time.

9. Cost effectiveness

Implementation of all above mentioned features will make the system very cost effective. Total cost will be much lower than in-center hemodialysis, and should successfully compete with any other method of chronic dialysis.

DESCRIPTION OF THE INVENTION

In accordance with this invention, hemodialyzer apparatus is provided which comprises the following:

Dialyzer membrane means is provided having first and second sides, as is of course conventional. Dialyzate flow path means are provided for passing dialysis solution across the first side of the membrane means, while blood flow path means are provided for passing blood across the second side of the membrane means for dialysis thereof.

A solution storage tank is connected to the dialyzate flow path means. Venous and arterial connector means are carried by the blood flow path means for alternative connection with the vascular system of a patient and with each other through a conventional shunt connector or the like. A water inlet conduit is provided, communicating with water treatment means for processing water from the inlet conduit to purify the water to a condition suitable for use in the hemodialysis apparatus.

A first conduit extends from the water treatment means to receive purified water therefrom. A second conduit is connected to the first conduit, and has means for carrying desired amounts of dialysis solution solutes, such as lactic acid, potassium chloride, magnesium chloride, calcium chloride, sodium chloride, and sodium bicarbonate.

Thus, a predetermined amount of purified water from the first conduit can pass through the second conduit and disperse the solutes, which may be conveyed with the water through further conduit means to the solution storage tank, to provide a desired quantity of the dialysis solution in a first operating mode.

A third conduit is also provided, being connected to the first conduit and having means for carrying desired amounts of hemodialyzer apparatus antimicrobial and cleaning agent, such as formaldehyde solutions, hydrogen peroxide, or the like. Thus, a predetermined amount of purified water from the first conduit can pass through the third conduit to disperse the antimicrobial and cleaning agent and to convey it through the further conduit means to the solution storage tank, to provide a desired quantity of antimicrobial cleaning solution in a second operating mode.

A fourth conduit is also preferably provided, connected to the dialyzate flow path means, and communicating with the blood flow path means, to provide antimicrobial cleaning solution, and also rinsing solution, to the blood flow path means in the second operating mode.

Also, valve and control means are provided to selectively and automatically provide and control fluid flow throughout the apparatus in its various stages of operation.

DESCRIPTION OF SPECIFIC EMBODIMENTS

Figure 1:
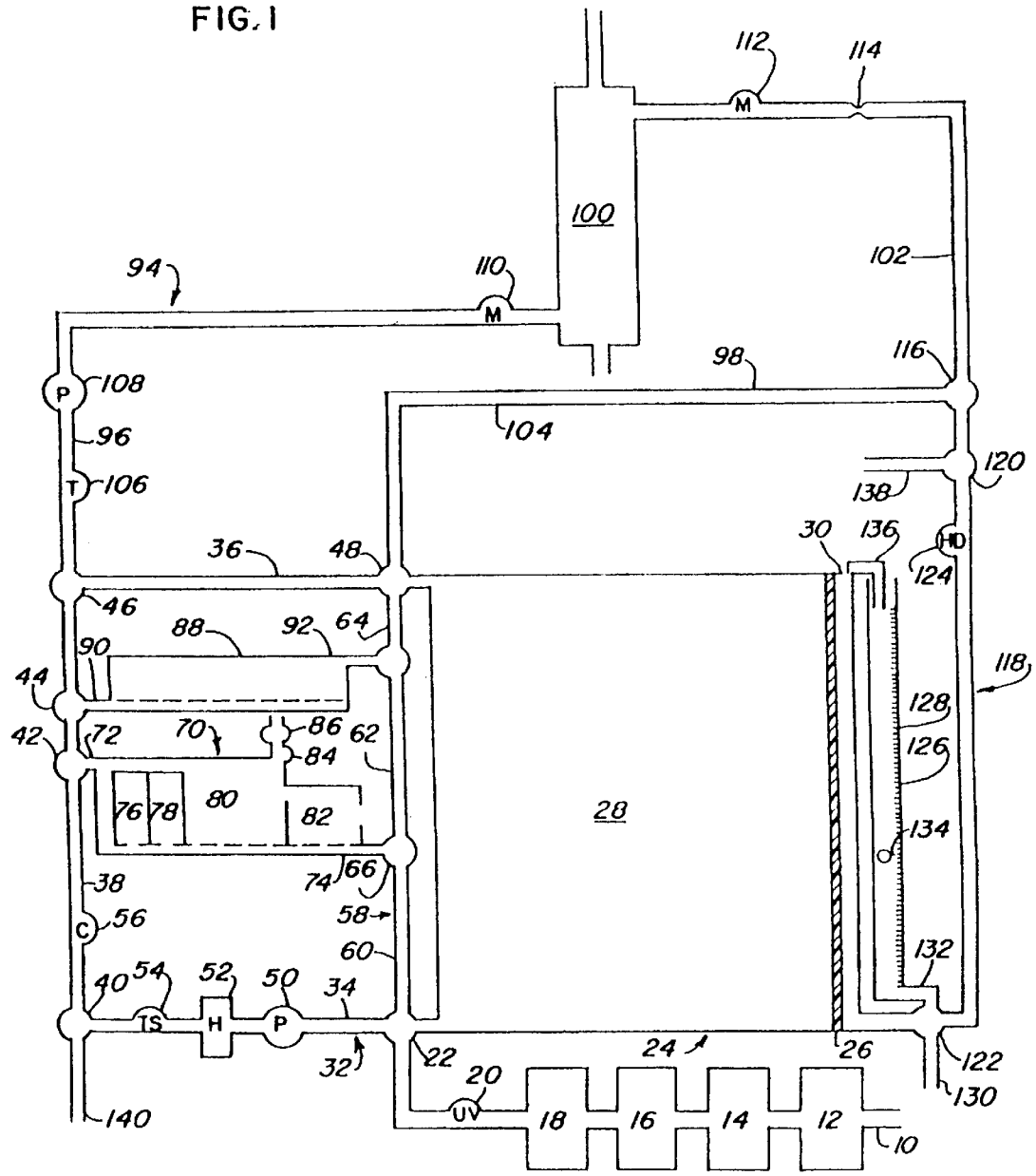
FIG. 1 is a diagrammatic view of the apparatus, showing the dialyzate flow path and other water flow paths.

The invention is a highly automated system which comprises a relatively simple hemodialysis system made of the following as shown in the drawings:

An integral water treatment line and system 10 comprises a coarse particulate pre-filter (if necessary) 12, a carbon adsorption filter 14, a reverse osmosis membrane 16, a deionizing cartridge 18, and UV light 20. Purified water enters the system through a valve 22.

A dialysis solution preparation and delivery system (FIG. 1) is provided, made of heat resistant materials, capable to withstand repeated cleanings, and comprising the following.

A 60–90 liter tank 24 has a diaphragm 26 separating a fresh dialysis solution compartment 28 from used dialysate compartment 30. The diaphragm is leak tight but can move freely so that the increase in capacity of one compartment is associated with the identical decrease in capacity of the other. As is shown in Sausse U.S. Pat. No. 4,029,059, for example, a corrugated, expansible membrane may be used.

A mixing/heating circuit 32 is provided for recirculating fluids in the dialysis solution compartment, heating water, and mixing the chemicals with water, comprising of inflow line 34, outflow line 36, and bridging lines 38, furnished with valves 22, 40, 42, 44, 46, 48, pump 50, heater 52 thermostat 54, and conductometer 56.

A bypass conduit 58 connects inflow line 34 and outflow line 36 of the mixing/heating circuit 32 through valves 22, 48 and comprising three lines 60, 62, 64 connected through valves 66, 68.

A salt chamber 70 for dialysis solution chemicals is provided with inflow and outflow tubings 72, 74 connected with the bridging line 38 of mixing/heating circuit 32 through valve 42, and with the bypass conduit 58 through unidirectional valve 66. The chamber 70 contains two cells for syringes, one with lactic acid and concentrate of potassium chloride 76, and the other with magnesium chloride and calcium chloride 78, and two cells for cartridges, one with dry, powdered sodium chloride 80 and the other with dry, powdered sodium bicarbonate 82. The chamber 70 is provided with a sensor of fluid level 84 and a vent with valve 86. The chamber 70 is water tight, but can be opened to add predetermined-weight changes of dry chemicals, specifically in the form of a cartridge provided to the user by the manufacturer.

A chemical chamber 88 is provided for adding cleaning/disinfecting mixture, with inflow and outflow tubings 90, 92 connected with the bridging line 38 of the mixing/heating circuit 32 through valve 44, and with the bypass conduit 58 through the valve 68. The chamber 88 accommodates a cartridge containing conventional chemicals which, when dissolved in water, produce chemical species which will both clean up the extracorporeal circuit of blood and blood elements and will disinfect all fluid circuits in the system. This chamber is also water tight, but can be opened for placing new charges of dry chemicals, also preferably as commercially manufactured cartridges.

Dialysis solution circuit 94 with inflow and outflow tubings 96, 98 is connected with the dialysate compartment of the hemodialyzer 100, and through the valves 46, 48 with the outflow tubing 36 of the mixing/heating circuit 32. Inflow tubing 96 is equipped with a thermometer 106, pump 108, and dialysis solution manometer 110. The outflow tubing 98, which comprises a proximal and distal segment 102, 104, is furnished with a dialysate manometer 112, dialysate clamp 114 for regulating dialysate pressure, and dialysate valve 116.

Dialysate tubing 118 carries used dialysate into the dialysate compartment 30 of the tank 24, being provided with valves 120, 122 and hemoglobin detector 124 for detecting free hemoglobin or red cells in the effluent dialysate as an indicator of blood leak in the fibers of the dialyzer.

A measuring cylinder 126 connected with drain pipe 130 through an outflow tubing 132 and valve 122. Cylinder 126 is provided with a scale 128 and a sensor 134 for respective visual and automatic determination of the fluid level. During hemodialysis the sensor 134 measures ultrafiltration rate to regulate ultrafiltration by pressure adjustment in the dialysate and blood compartments of the dialyzer. Cylinder 126 is filled with fluids through outflow tubing 136 of the dialysate compartment 30.

A blood/dialysate shunt 138 is provided for connection with an extracoporeal blood circuit, being controlled by valve 120.

Drain pipes 130, 140 are also provided.

Figure 2:
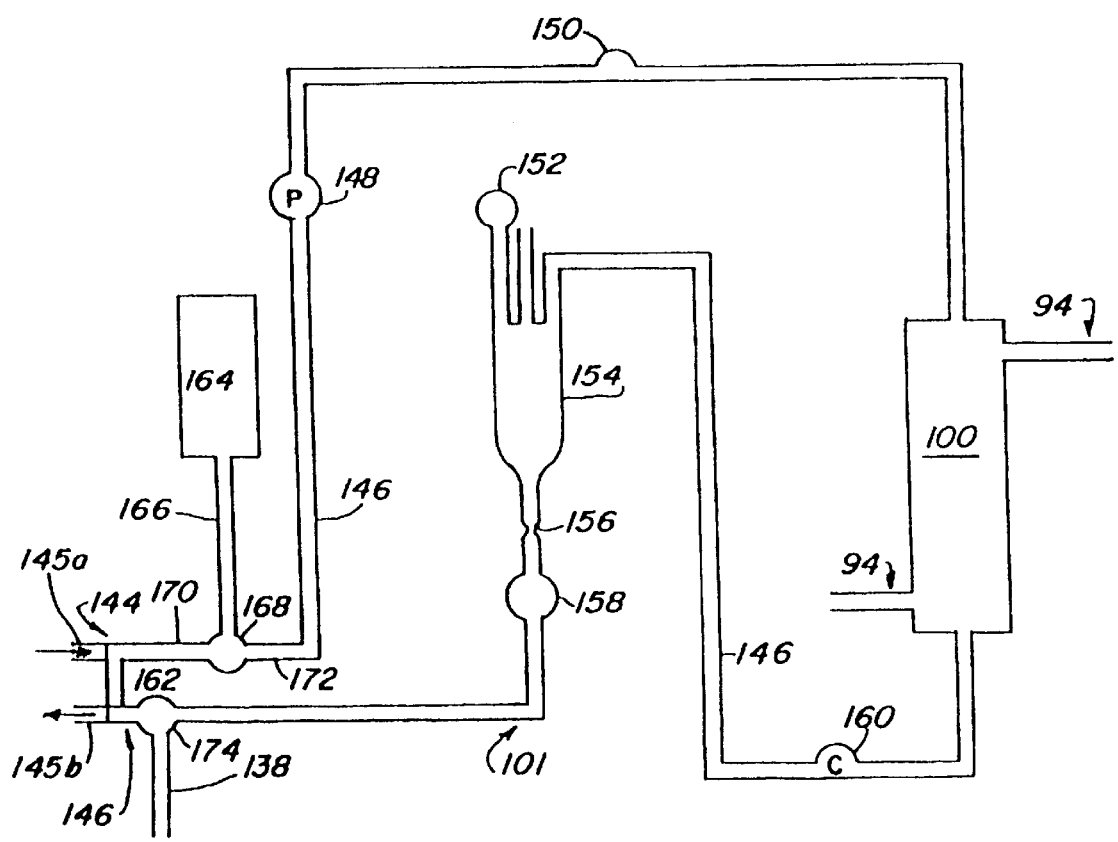
FIG. 2 is a diagrammatic view of the blood flow path portion of the apparatus.

The extracorporeal blood circuit 101 (FIG. 2) is made of materials designed to withstand repeated cleanings and to be as biocompatible and non-thrombogenic as possible, and includes the following.

A hemodialyzer 100, is provided, preferably with high flux and high biocompatibility characteristics.

Inflow and out flow lines 144, 146 are provided, being for connection with respective inflow and outflow lumens 145*a*, 145*b* of preferably a double lumen intravenous catheter implanted in the patient.

A blood pump 148 is provided for moving blood or other fluids within the extracorporeal circuit.

Blood manometers 150, 152 are for determining the pressure in the lines (both inflow and outflow), at the post-pump pre-dialyzer location, and at the post-dialyzer location.

An air trap 154 is present in the outflow line 146 prior to blood returning to the patient.

A blood clamp 156 regulates pressure in the blood compartment of the hemodialyzer 100.

An air/foam detector 158 in the outflow line between the air trapping chamber and the patient for closing the line if foam is present.

A detector 160 is provided for detecting the conductivity of any solution in the circuit.

A coupling means 162 to connect the inflow and outflow blood lines 144, 146 in a closed loop is present adjacent the location of the lumens 145 of the patient's catheter or arteriovenous shunt.

A saline bag 164 and conduit 166 connects the bag to the inflow line 144 of the extracorporeal circuit through a saline valve 168. The valve 168 divides the inflow line 144 into proximal and distal segments 170, 172.

An unidirectional blood/dialysate shunt valve 174 connects the outflow line 146 with the dialysate tubing 118 through blood/dialysate shunt 138 and valve 120. The shunt valve 174 allows fluids to pass from the extracorporeal blood circuit into the dialysate effluent tubing 118, but prevents fluid passage in the opposite direction.

A microprocessor-based monitoring and controlling system may be provided which contains all the logic, receives and processes all commands by controlling valves and pumps, monitors and interprets all sensors, activates all alarms, and directs the operation of all aspects of the system.

A video display may also be provided with associated electronics, processors and keypads for all communication into and out of the machine.

The first step in this highly automated dialysis procedure is for the system to automatically prepare a fresh batch of dialysis solution for the upcoming treatment. At the end of the previous treatment, the patient has done three things in preparation for the next treatment. First, he/she sterilizes and cleans manually the salt chamber 70, and inserts syringes with solutions and cartridges with dry chemicals into appropriate cells. Secondly, the patient inserts an appropriate cartridge into the chemical chamber 88. Thirdly, the patient programs into the system's memory (via a touch-sensitive display) the time of day he/she intends to begin the next treatment. This last step will often not be necessary, however, since many patients will dialyze at the same time every day, and will need only to enter this time once and change it thereafter by exception only. All these tasks will take only a few minutes.

Knowing the expected start time of the next treatment, the system will begin preparation of the dialysis solution so that it will be fully mixed, and its quality assured, just before the patient is ready to begin, thereby minimizing bacterial growth. The salt chamber 70, dialysis solution compartment 28, dialysate compartment 30, dialysate tubing 118, and measuring cylinder 126 are empty at this time. As will be the case in subsequent modes of operation, water can only enter the blood flow path by passing, first, through an R/O membrane 16 whose integrity is continuously assured by conductivity; second, through a UV light chamber 20; and finally, through the hemodialyzer 100 whose membrane is restrictive to pyrogens, and whose integrity is assured by the blood leak detector. In this way, the system essentially guarantees that no bacteria or pyrogens will ever enter the patient via this route.

The process starts after internal washing with cleaning solution in the previous cycle, plus draining all fluid present in the chemical chamber 88, mixing/heating circuit 32, bypass conduit 58, and hemodialyzer dialysis solution circuit 94. The system is first flushed with sufficient purified water from line 10 so that any cleaning/disinfecting agents and contaminants remaining from the previous treatment are removed. After emptying again, the chamber 88, circuits 32 and 94, and bypass conduit 58 are filled with water from line 10. Both circuit pumps 50 and 108 are activated so that the pressure in the hemodialyzer dialysis solution circuit 94 is raised, thus pushing water through the hemodialyzer membrane into the blood flow path 101 and dislodging any remaining blood elements or chemicals. The blood/dialysate shunt valve 174 (FIG. 2) allows fluid to flow through the shunt 138 into dialysate tubing 118 for drainage. This process continues for a predetermined time. Then the blood pump 148 recirculates the fluid left in the blood flow path 101 in a countercurrent direction to the circulating water in the dialyzate flow path 94. Owing to the concentration gradient, any remaining chemicals from the blood flow path 101 will diffuse into the water in hemodialyzer dialysis solution circuit 94. The valves 116, 120, and 122 direct the water to the drain pipe 130. Once conductometer 160 shows that there are no chemicals left in the extracorporeal circuit, the blood/dialysate shunt valve 174 closes, and all water is drained from the whole dialysis solution preparation and delivery system of FIG. 1.

At a predetermined time before the next use, the dialysis solution compartment 28 of the tank 24 is filled with purified water through line 10. The diaphragm 26 is pushed by the water to maximize capacity of the dialysis solution compartment 28 and minimize capacity of the dialysate compartment 30. Valves 22, 40, 42, 44, 46, 48, 66, 68, 116, 120, and 122 are arranged in such positions that water fills the mixing/heating conduit 32, bypass conduit 58, hemodialyzer dialysis solution circuit 94, dialysate tubing 118, and dialysate compartment 30 of the tank 24. The measuring cylinder 126, and both chambers 70 and 88 remain fluid free at this time, as controlled by valves 42, 44 and 122. Then after the above enumerated circuits, conduits, tubings and compartments are completely filled with water, water enters the measuring cylinder 126 through the outflow tubing 136, and the sensor 134 in the measuring cylinder 126 causes the valve 22 to close. Then the valves 46 and 48 close entrance into the hemodialyzer dialysis solution circuit 94. Pump 50 is activated to circulate water in the mixing/heating circuit 32 which includes lines 34, 38, 36, and dialysis solution compartment 28 of the tank 24. The water is warmed by the heater 52 to the desired temperature set on the thermostat 54.

Once the desired temperature is achieved, valve 42 directs water through the tubing 72 into the salt chamber 70, and the air is expelled through the vent 86. Once the water fills completely the chamber as indicated by the sensor 84, the vent 86 is closed, and the valve 66 assumes such a position as to allow water flow through the chamber 70 and outflow tubing 74 into the bypass conduit 58 to tank compartment 28. The depletion of fluid in the dialysis solution compartment as chamber 70 fills causes the diaphragm 26 to move and to lower the level of fluid in the dialysate compartment 30.

As water passes through chamber 70, lactic acid and concentrates are automatically injected from the syringes 76, 78 into the water, and the cartridges 80, 82 with powdered chemicals are automatically opened and mixed with the flowing water. Recirculation of fluid continues for a predetermined time to guarantee complete dissolution of dry chemicals.

Once the correct concentration of dialysis solution electrolytes is assured by conductometer 56, valve 42 closes the inflow tubing 72 of the chamber for dialysis solution chemicals 70. Air vent 86 opens, and the fluid is completely drained from the chamber. The diaphragm 26 is thus moved to overfill the dialysate compartment 30 which activates sensor 134 in the measuring cylinder 126. The sensor 134 causes the valve 66 and vent 86 to close.

Then, the valves 46 and 48 open the dialysis solution circuit 94. The pump 108 is activated, and the dialysis solution is circulated, in a closed loop fashion, through the hemodialyzer 100, along lines 102, 104, and 58 back into the mixing/heating circuit 32. Then the solution flows through lines 38, 96 to complete the circuit.

Simultaneously, the sterile water left in the blood flow path 101 by the previous flushing step is recirculated in a countercurrent direction to the dialysate using the blood pump 148. Owing to the concentration gradient, electrolytes from the dialysate will diffuse through the dialysis membrane into blood flow path 101 until the concentration of all ionic species is in equilibrium. The extracorporeal circuit is thus automatically primed with sterile, non-pyrogenic, physiologic solution. This process takes just a few minutes and, during this time, the rate of conductivity rise in the extracorporeal circuit is monitored by conductometer 160 and used to establish first the clearance properties of the dialyzer. This, in turn, is used to determine when the performance of dialyzer 100 has decayed to a point that it should be replaced, and second, when equilibrium is achieved and priming is complete.

An electronic display will indicate to the patient that priming is complete, and that it is possible to start dialysis. The patient opens both solute chambers 70 and 88, drains residual fluid (if present), inspects whether all chemicals have been completely dissolved, and removes spent cartridges and syringes. If the inspection verifies proper machine function, the patient measures his/her weight, blood pressure, pulse and temperature, and enters data into a flow-sheet and the system memory together with intended ultrafiltration, duration of dialysis, blood and dialysate flow. Then the patient removes spent saline bag 164 and replaces with a new one, and touches the display to activate the saline flushing cycle. The machine drains a predetermined amount of saline through the saline conduit 166 and valve 168, coupling means 162, blood dialysate shunt valve 174 and shunt 138 into dialysate tubing 118 to flush the freshly made connection from possible contaminants, and then changes position of the saline valve 168.

The patient activates the blood pump 148 to flush more saline through the hemodialyzer 100 and into the blood/dialysate shunt 138. The patient opens inflow and outflow lumens of his catheter 145, which typically may be of the intravenous double lumen type so that needle sticks are not required. The patient assures the free flow of blood, and injects heparin into both lumens. Finally, the patient removes the coupling means 162 from the inflow and outflow lines 144, 146, and connects the lines to his/her catheter inflow and outflow lumens 145, using aseptic technique. When the connections are made, the patient touches the control display to so indicate.

The machine now begins to draw blood into the arterial blood line 144 while the priming solution is directed through the blood/dialysate shunt 138 to dialysate tubing 118. After a predetermined amount of blood is drawn into the circuit, the priming solution is directed back to the patient by means of valve 174 to prevent any blood loss through the blood/dialysate shunt 138. As an additional security measure, the hemoglobin detector 124 will stop the blood pump 148 if any blood or hemoglobin enters the dialysate tubing 118. Finally, the patient observes the function of the blood/dialysate shunt valve 174 and can stop the procedure manually if blood enters the blood/dialysate shunt 138.

The measuring cylinder 126 (FIG. 1) is emptied through the outflow tubing 132, valve 122, and the drain pipe 130 at that time. The speed of pump 148 is increased to the prescribed value. Valves 48 and 116 shut off return of dialysate to circuit 32 and direct spent dialysate into the dialysate tubing 118. The dialysis solution is pumped single-pass through the dialysate compartment of the dialyzer, countercurrently to the blood flow, and then into the spent dialysate compartment 30 of the tank 24 through the dialysate tubing 118 for measuring volume. An increase of fluid volume coming out of dialyzer 100 over the fluid volume going into dialyzer 100 can be measured in cylinder 126 to monitor ultrafiltration. In the case where hypotension is detected by patent's prodromal symptoms and confirmed by blood pressure measurement, the blood from the dialyzer will be returned to the patient through the outflow line 146 and sterile saline will be drawn from the bag 164 into inflow line 144. This saline addition continues until the pressure normalizes, and the normal dialysis procedure can continue. With daily treatments and controlled ultrafiltration, the incidence of hypotension will be virtually eliminated in most patients as described above.

At a predetermined time the display alerts the patient that the treatment is completed. The patient touches the display to initiate the process of dialysis termination. The blood pump 148 stops. The saline valve 168 connects the saline conduit 166 exclusively with inflow line 144, and the saline from the bag 164 pushes blood back to the patient through the proximal segment 170 of the inflow line 144 and the inflow lumen 145a of the patient's catheter. After a predetermined volume of saline is infused, the saline valve 168 closes the connection of the saline conduit 166 with the proximal segment 170 and opens connection of the conduit 166 exclusively with the distal segment of the inflow tubing 172. The blood pump 148 is activated. As the remaining blood is pumped, pump 148 pulls saline into the distal segment 172 of the inflow line 144, the blood compartment of hemodialyzer 100, the outflow line 146, and back into the patient through the outflow lumen 145b of the patient's catheter. In the meantime, the patient clamps the inflow lumen 145a of the patient's catheter. After predetermined volume of saline is infused, the blood pump 148 is stopped. The patient controls the process of blood return and can correct it manually, if needed.

When no blood is visible in the outflow line 146 the patient clamps the outflow lumen 145b of his catheter, disconnects the system tubing, and touches the display to indicate that the process of cleaning/disinfecting may be initiated.

The machine automatically starts the process of cleaning. In the meantime the patient fills both of his catheter 145 lumens with heparin, secures both lumens with clamps and caps, measures his/her weight, blood pressure, pulse, temperature, and total ultrafiltration and enters data into the flow/sheet and the system memory. Finally, as mentioned earlier, the patient sterilizes and cleans manually the chambers 70, 88, inserting syringes with solutions and cartridges with dry chemicals into appropriate cells. The patient also inserts an appropriate cartridge into the cleaning chemical chamber 88, and programs the time of day of the intended next treatment.

The process of cleaning starts by creating high pressure on the dialysis solution side of dialyzer 100, thus pushing solution through the dialyzer membrane and dislodging blood elements that may have accumulated in the pores or on the membrane during the treatment. Blood/dialysate shunt valve 174 directs fluid in blood circuit 101 through the shunt 138 into dialysate tubing 118. This process continues until a predetermined volume of dialysate has been used to flush the extracorporeal circuit. Finally a remaining volume of saline from bag 164 is flushed through the blood compartment of the hemodialyzer 142 to remove the dislodged blood elements and rinse them toward shunt 138 and ultimately drain 130.

Next, the blood/dialysate shunt 138 is closed, and all fluid is drained from the whole dialysis solution delivery system by setting valves in appropriate positions. Then, the dialysis solution compartment 28 of the tank 24 is filled with purified water from line 10. The diaphragm 26 is pushed by the water to maximize capacity of the dialysis solution compartment 28 and to minimize capacity of the dialysate compartment 30. Valves 22, 40, 42, 44, 46, 48, 66, 68, 116, 120, and 122 are arranged in such positions that water fills the mixing/heating conduit 32, bypass conduit 58, hemodialyzer 10, dialysis solution circuit 103, dialysate tubing 118, and dialysate compartment 30. The measuring cylinder 126, and both chambers 70 and 88 for chemicals remain fluid free at this time. Once the desired circuits, conduits, tubings and compartments are completely filled with water, the sensor 134 in the measuring cylinder 126 causes the valve 22 to be shut. Then the valves 46 and 48 close entrance into the hemodialyzer dialysis solution circuit 94, and pump 50 is activated to recirculate water in the mixing/heating line 32, conduit 38 and dialysis solution compartment 28. The water is warmed by the heater 52 to the desired temperature set on the thermostat 54. Once the desired temperature is achieved, valve 44 directs water through the inflow tubing 90 into chemical chamber 88, and then through the outflow tubing 92 and valve 68 into the bypass conduit 58 and then compartment 28. Recirculation of fluid continues for a predetermined time to guarantee complete dissolution of dry chemicals from chamber 88.

Once the dissolution of the chemicals is assured by conductometer 56, valves 46 and 48 open the hemodialyzer dialysis solution circuit 94. Pump 108 is activated, and the dialysis solution is recirculated, in a closed loop fashion, through hemodialyzer 100 and through the mixing/heating circuit 32. Simultaneously, the saline left in blood flow path 101 circuit by the previous flushing step is recirculated in a counter current direction to the dialysate using the blood pump 148. Owing to the concentration gradient, cleaning/disinfecting chemicals from the dialysate will also diffuse into blood flow path 101 until the concentration of all solutes is in equilibrium. The dialysate valve 116 allows passage of fluid into dialysate tubing 118 and dialysate compartment 30 of the tank to flow countercurrently to the fluid in the blood compartment of the hemodialyzer. After total amount of fluid is transferred from the dialysis solution compartment 28 into the dialysate compartment 30, the dialysis solution compartment 28, heating/disinfecting circuit 32, and bypass conduit 58 are drained, and flushed twice with water through appropriate positions of valves 22, 40, 48, 66, 68, and 86.

Finally the pump 50 is activated to recirculate water in the mixing/heating circuit 32, bypass conduit 58, and dialysis solution compartment 28 of the tank 24, and the water is warmed by the heater 52 to the desired temperature set on the thermostat 54. Once the desired temperature is achieved, the positions of valves 22 and 48 are changed to allow complete drainage of water from the dialysis solution compartment 28. Finally, the valves 22 and 48 completely close the dialysis solution compartment. At this instant the dialysate compartment 30 and measuring cylinder 126 are drained completely of fluids. The position of the valves 22, 48, 116, 120, and 122 is changed to allow more water to enter into and recirculate in the mixing/heating circuit 32 bypass conduit 58, and pass through distal segment 104 of the outflow tubing 102 of the hemodialyzer dialysis solution circuit 94, into dialysate compartment 30. Once the dialysate compartment is overfilled with water, the valves 22, 44, 46, 48, and 68, change positions to allow fluid to recirculate in mixing/heating circuit 32, bypass conduit 58, and the chamber for cleaning/disinfecting chemicals 88. The solution present in this chamber still contains cleaning/disinfecting chemicals and becomes slightly diluted. The position of valves 46, 48, and 116 changes again so that the solution will slowly recirculate in the mixing/heating circuit, bypass conduit 58, and hemodialyzer dialysis solution circuit 94. Also, the blood pump 148 will slowly recirculate the fluid in blood flow path 101. The presence of disinfectant and fluid movement restrains bacterial growth, and continues until the time of the next treatment.

Typically after one month of use, the whole extracorporeal blood circuit is replaced by a new one. The frequency of replacement of water treatment filters will depend on the local-quality of water.

Optionally the system may be provided with automated vital signs and machine monitoring equipment. These may be connected with a central monitoring service (or dialysis facility) to remotely monitor the patient and the instrument during the treatment, thereby obviating the need for a partner in most cases.

The inflow line 96 of the hemodialyzer dialysis solution circuit 94 may be provided with a depyrogenation filter.

Powdered glucose may be used additionally for dialysis solution preparation.

Ozone may be used as disinfecting agent, and an ozone generator may be included in the cleaning/disinfecting chamber.

The salt chamber may be cleaned and sterilized automatically. In such a case the patient inserts syringes and cartridges into the salt chamber 8–12 hours after termination of dialysis.

I have been interested in an influence of dialysis frequency on symptoms of uremia for many years. In 1974 and 1975, I published three papers dealing with the adequacy of hemodialysis (Twardowski Z: "The adequacy of hemodialysis in treatment of chronic renal failure." Acta Med Pol 1974; 15: 227–243. Twardowski A: "Significance of certain measurable parameters in the evaluation of hemodialysis adequacy." Acta Med Pol 1974; 14: 245–254. Twardowski A: "Effect of long-term increase in the frequency and/or prolongation of dialysis duration on certain clinical manifestations and results of laboratory investigations in patients with chronic renal failure." Acta Med Pol 1975; 16: 31–44.).

I have always observed improvement in the patient's well-being with an increase in frequency of dialysis. The results were so impressive I concluded the last paper of this series with the statement: "It seems that daily short-lasting dialysis will be, in the near future, the basic form of treatment of uremia." In these studies, I did not try more than four weekly dialyses.

In later years, I applied daily short dialysis in many patients, but only in connection with the additional stress of surgery, trauma, or infection and daily dialysis was applied usually for only one or two weeks.

Teschan et al. (Teschan P E, Ahmad S, Hull A R, Nolph K D, Shapiro F I: "Daily dialysis—applications and problems." Trans Am Soc Artif Intern Organs 1980; 26: 600–602.) explored theoretically the rationale and technical and logistical requirements for implementation of daily dialysis. They concluded that it "is not routinely indicated by available information and experience in either acute or chronic renal failure;" however, they stressed that "On the other hand it may be helpful if feasible and does not result in injury to patients or produce depletion syndrome or other evidence of illness."

Extensive evaluation of daily dialysis have more recently been performed by Buonacristiani et al. (Buonacristiani U, Quintaliani G, Cozzari M, Giombini L, Ragaiolo M: "Daily dialysis: Long term clinical metabolic results." Kidney Int. 1988; 33 (suppl 24): S137–S140.). These studies showed an excellent intra-dialytic tolerance with dramatic decreases in most symptoms of dialysis, including incidence of hypotension, cramps, headaches, and asthenia. Blood pressure normalized in all patients, hematocrit increased, and nerve conduction velocity slowly improved. All patients enjoyed improved general well-being, increased appetite and muscular strength, and some patents reported improved sexual function. The evolution of CAPD in the late 1970's and early 1980's was widely hailed for its ability to decrease some of the same symptoms. However, the improvement effected by CAPD over three times weekly HD pales in comparison to the improvement demonstrated by Buonacristiani, et al.

A striking improvement in intradialytic tolerance during daily hemodialysis has also been reported by Hombrouckx et al. (Hombrouckx R, Bogaert A M, Leroy F, Beelen R, de Vos J Y, Van Overmeeren G, Verhoeven R, Verdonck P, Vercruysse V: "Limitations of short dialysis are the indications for ultrashort daily auto dialysis.: ASAIO Trans 1989; 35: 503–505.).

Recently I have started a study in three patients to compare the clinical and metabolic consequences of change from routine chronic, thrice weekly hemodialysis to daily hemodialysis. Similar to others, I observed a dramatic improvement in general well-being, almost complete disappearance of all symptoms of intradialytic intolerance and post dialysis weakness. During the 6 months of daily hemodialysis schedule (504 treatment sessions) only 19 (3.8%) mild hypotensive episodes occurred in these 3 patients, where during the preceding 3 months (144 treatment sessions) 23 (16%) of such episodes, including 3 (2.1%) severe "crashes", were noted. Again, dramatic improvements in control of blood chemistries and blood pressure were observed.

Owing to the automation, the time and effort involvement on the part of the patient will be drastically reduced. The machine does most of the work. Eliminated or markedly simplified are:

The time traveling to and from the dialysis clinic,

Mixing of dialysate,

Assembly of the extracorporeal circuit,

Priming of the extracorporeal circuit,

Recirculating priming solution to dialyze, away reuse contaminants.

Testing for residual disinfectant,

Manual rinseback of blood,

Disassembly of the extracorporeal circuit,

Manual reuse of the dialyzer and bloodlines,

Cleaning and disinfecting the plumbing,

Cleaning and disinfecting the water treatment system.

Also, if the patient is employing a permanent catheter instead of needles, there will be no need to (painfully) insert them or to hold a compress on the puncture sites at the end of the treatment and wait until clotting occurs. In addition, the catheter should yield faster blood flow rates and fewer negative pressure alarms and therefore shorter treatment times.

The involvement of a partner can be eliminated completely or at the very least reduced significantly because of:

No needles to insert,

Reduced Symptoms,

Optional remote vital signs monitoring and machine control system.

The time, intelligence, and motivation required to learn the operation of the instrument and the dialyzing procedures are significantly reduced.

The system's self-contained compact design would allow travel.

The space in the patient's home previously required for supplies, water treatment system, and dialysis machine are significantly reduced.

The small batch, positive pressure design will eliminate many complicated subsystems of current dialysis instruments and should therefore, result in a much more reliable system. Use of dry chemicals instead of concentrates decreases cost and saves storage space.

The automation inherent in the design as well as the user friendly display will significantly enhance learning and operating the system.

The integrated water treatment system and compact size should allow portability and therefore travel.

The above has been offered for illustrative purposes only, and is not to be interpreted as limiting the scope of the invention, which is as described in the claims below.

That which is claimed is:

1. A method for flushing and filling of an extracorporeal blood circulation system of a dialysis machine, said machine having a dialyzer, a separate dialysis liquid circuit flowing through a dialysate side of the dialyzer, with the extracorporeal blood circulation system flowing through a blood side of the dialyzer for removal of impurities from the blood, the dialysate and blood sides of said dialyzer separated by a hemodialyzer membrane, said method comprising the steps of:

transporting dialysis liquid from the dialysis liquid circuit in the dialysate side of the dialyzer, through said hemodialyzer membrane into said blood side of said dialyzer and the extracorporeal blood circulation system to flush and fill said system, and conducting a dialysis treatment.

2. The method according to claim 1 wherein dialysis liquid is passed through said dialyzer and is thereby filtered.

3. The method according to claim 1, wherein said dialysis machine has a blood pump and wherein dialysis liquid is pumped by said blood pump into said extracorporeal blood circulation system.

4. The method according to claim 1, wherein the dialysis liquid circuit comprises a pump, and wherein the dialysis liquid is pumped by said pump into said extracorporeal blood circulation system.

5. The method of claim 1, wherein said dialysis machine has a filling program for filling the dialysis circuit, and wherein the step of transporting dialysis liquid through the extracorporeal blood circulation system is initiated by said filling program.

6. The method of claim 1 wherein the blood circulation system is flushed and filled prior to the dialysis treatment.

7. The method of claim 1 wherein the blood circulation system is flushed and filled after completion of the dialysis treatment.

8. A method of flushing the extracorporeal blood circulation circuit of a dialysis machine, said machine comprising a dialyzer with the blood circulation circuit passing through one side of the dialyzer, and a dialysis liquid circuit containing dialysis liquid passing through the other side of the dialyzer, said method comprising the steps of pumping dialysis liquid from the dialysis liquid circuit through the dialyzer and into the blood circuit the method comprising the steps of pumping dialysis liquid from the dialysis liquid circuit through the dialyzer and into the blood circuit.

* * * * *